(12) United States Patent
Komuro (10) Patent No.: US 10,987,182 B2
(45) Date of Patent: Apr. 27, 2021

(54) MEDICAL MANIPULATOR SYSTEM AND METHOD FOR CONTROLLING A MEDICAL MANIPULATOR

(71) Applicant: OLYMPUS CORPORATION, Tokyo (JP)

(72) Inventor: Takahiro Komuro, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 386 days.

(21) Appl. No.: 16/045,821

(22) Filed: Jul. 26, 2018

(65) Prior Publication Data

US 2018/0344418 A1    Dec. 6, 2018

Related U.S. Application Data

(63) Continuation of application No. PCT/JP2016/052289, filed on Jan. 27, 2016.

(51) Int. Cl.
*A61B 17/00* (2006.01)
*A61B 34/30* (2016.01)
(Continued)

(52) U.S. Cl.
CPC ........ *A61B 34/74* (2016.02); *A61B 17/00234* (2013.01); *A61B 17/3423* (2013.01);
(Continued)

(58) Field of Classification Search
CPC .............. A61B 17/00234; A61B 34/74; A61B 17/3423; A61B 34/30; A61B 2034/303; A61B 2034/305; A61B 2090/064
See application file for complete search history.

(56) References Cited

U.S. PATENT DOCUMENTS

2003/0040737 A1*  2/2003  Merril ................... A61B 34/70
                                                         606/1
2007/0078301 A1*  4/2007  Kura ...................... A61B 10/06
                                                         600/106
(Continued)

FOREIGN PATENT DOCUMENTS

JP       2008-212349 A      9/2008
JP       2015-024032 A      2/2015
WO    WO 2015/137040 A1     9/2015

OTHER PUBLICATIONS

International Search Report dated Mar. 8, 2016 issued in PCT/JP2016/052289.

*Primary Examiner* — Stephen Holwerda
(74) *Attorney, Agent, or Firm* — Scully, Scott, Murphy & Presser, P.C.

(57) ABSTRACT

A medical manipulator system includes: a treatment tool including an arm with joints and an end effector provided at a distal end of the arm; an insertion aid device; an advancement/retraction driving unit configured to drive the treatment tool to be advanced/retracted in the insertion aid device; an advancement/retraction operation unit configured to drive the advancement/retraction driving unit; a stopper configured to limit an operation of the advancement/retraction driving unit by actuation; an interference detector configured to be capable of detecting interference between an arm unit projected out of the insertion aid device and the insertion aid device; and an operation instruction unit configured to be capable of actuating the stopper. The operation instruction unit limits retraction movement of the treatment tool with respect to the insertion aid device by actuating the stopper.

14 Claims, 9 Drawing Sheets

(51) Int. Cl.
- *A61B 34/00* (2016.01)
- *A61B 17/34* (2006.01)
- *A61B 90/00* (2016.01)

(52) U.S. Cl.
CPC ........ *A61B 34/30* (2016.02); *A61B 2034/303* (2016.02); *A61B 2034/305* (2016.02); *A61B 2090/064* (2016.02)

(56) References Cited

U.S. PATENT DOCUMENTS

| | | | | |
|---|---|---|---|---|
| 2007/0112255 | A1* | 5/2007 | Ikeda | A61B 1/0016 600/146 |
| 2008/0146875 | A1* | 6/2008 | Noguchi | A61B 1/31 600/117 |
| 2009/0105726 | A1* | 4/2009 | Sugiyama | A61B 1/0051 606/130 |
| 2010/0160728 | A1* | 6/2010 | Yoshie | A61B 1/00147 600/109 |
| 2013/0123597 | A1* | 5/2013 | Rothenberg | A61B 5/065 600/374 |
| 2014/0257327 | A1 | 9/2014 | Olson et al. | |
| 2017/0265890 | A1* | 9/2017 | Page | A61B 17/3423 |

\* cited by examiner

FIG. 11

MEDICAL MANIPULATOR SYSTEM AND METHOD FOR CONTROLLING A MEDICAL MANIPULATOR This application is a continuation application based on a PCT International Application No. PCT/JP2016/052289, filed on Jan. 27, 2016. The content of the PCT International Application is incorporated herein by reference.

FIELD OF THE INVENTION

The present invention relates to a medical manipulator system and a method for controlling a medical manipulator.

DESCRIPTION OF RELATED ART

Conventionally, a medical manipulator manipulated by an operator in a state in which observation means and a plurality of treatment tools are inserted into the body is known.

When this medical manipulator is introduced into the body, the medical manipulator is sometimes introduced with the observation means and the treatment tool inserted through an overtube. With this constitution, the introduction of the observation means and the treatment tool is completed by inserting one overtube only, and thus there is an advantage that an introduction procedure is simplified.

When the observation means and the treatment tool are inserted through an overtube and introduced into the body, the observation means and the treatment tool are used after being projected out of an opening at a distal end of the overtube when a procedure is performed.

In the medical manipulator, when the treatment tool is mounted on an arm having joints, a more complicated procedure can be performed compared to when only the treatment tool is projected out of the overtube. However, when the arm is retracted relative to the overtube in a state in which the joints of the arm are bent in a non-linear shape, the arm and the overtube interfere with each other. When the arm is further retracted in an interfering state, the arm or the treatment tool may be damaged, or the arm or the treatment tool may perform an unintended motion.

In connection with the above problem, a technique in which, when active forceps having a plurality of joints are inserted through a forceps channel of an endoscope and are used, states of the joints are switched according to whether or not the joints are located inside the forceps channel is disclosed in Japanese Unexamined Patent Application, First Publication No. 2008-212349.

In the technique disclosed in Japanese Unexamined Patent Application, First Publication No. 2008-212349, which joint or grasper is located outside the forceps channel is detected on the basis of information about a rotation angle of a forceps roller that advances/retracts the active forceps, a length dimension of the forceps channel, a length dimension of the active forceps, and positions of the joints and the grasper. A joint or a grasper located outside the forceps channel is controlled to be an operable state by manipulation of the forceps master arm, and a joint or the like located inside the forceps channel is controlled to be a released state in which it is not manipulated by the forceps master arm. A region in which the joint is in the release state is caused to conform to a shape of the forceps channel.

SUMMARY OF THE INVENTION

A first aspect of the present invention is a medical manipulator system, which includes: a treatment tool including an arm with joints and an end effector provided at a distal end of the arm; an insertion aid device through which the treatment tool is inserted; an advancement/retraction driving unit configured to drive the treatment tool to be advanced/retracted in the insertion aid device; an advancement/retraction operation unit configured to drive the advancement/retraction driving unit to perform an advancement/retraction operation of the treatment tool; a stopper configured to limit an operation of the advancement/retraction driving unit by actuation; an interference detector configured to be capable of detecting interference between an arm unit projected out of the insertion aid device and the insertion aid device; and an operation instruction unit configured to be capable of actuating the stopper. The operation instruction unit limits retraction movement of the treatment tool with respect to the insertion aid device by actuating the stopper to regulate the operation of the advancement/retraction driving unit when the interference detector detects the interference.

The interference detector may be configured to determine that the interference occurs when an external force greater than or equal to a predetermined value acts on the joints and acts in a direction in which the external force reduces the interference.

The interference detector may be configured to determine that the interference occurs when an external force greater than or equal to a predetermined value acts on the joints and when the advancement/retraction driving unit is driven in a direction in which the advancement/retraction driving unit retracts the treatment tool with respect to the insertion aid device.

The interference detector may be configured to determine that the interference occurs when an external force greater than or equal to a predetermined value acts on the joints.

The medical manipulator system of the present invention may further include: an advanced/retracted position detector configured to be capable of detecting a position of the advancement/retraction driving unit; and a storage unit configured to be capable of storing advanced/retracted position information detected by the advanced/retracted position detector. The interference detector may store the advanced/retracted position information when the interference is detected in the storage unit, and the operation instruction unit may actuate the stopper when advanced/retracted position information subsequently acquired by the advanced/retracted position detector satisfies a predetermined relationship with respect to the advanced/retracted position information stored in the storage unit.

A second aspect of the present invention is a medical manipulator system, which includes: a treatment tool including an arm with joints and an end effector provided on the arm; an insertion aid device through which the treatment tool is inserted; an advancement/retraction driving unit configured to drive the treatment tool to be advanced/retracted in the insertion aid device; an advancement/retraction operation unit configured to perform an advancement/retraction operation of the treatment tool; a stopper configured to be capable of regulating an operation of the advancement/retraction driving unit; a force sensor configured to be capable of detecting interference between the arm projected out of the insertion aid device and the insertion aid device; and a control unit configured to operate the stopper to regulate the operation of the advancement/retraction driving unit on the basis of detection information of the force sensor and to perform control to limit retraction movement of the treatment tool with respect to the insertion aid device.

A third aspect of the present invention is a method for controlling a medical manipulator, which includes: manipulating a treatment tool using a manipulation arm manipulated by an operator; detecting, by a sensor, when the treatment tool is manipulated to interfere with an overtube through which the treatment tool is to be inserted; and controlling, by a controller, an advancement/retraction driving unit, which drives the treatment tool to be advanced/retracted in the overtube, on the basis of information detected by the sensor.

In the method for controlling a medical manipulator of the present invention, when an external force greater than or equal to a predetermined value acts on joints provided on the treatment tool and acts in a direction in which the external force reduces interference between the joints and the overtube, the controller may control the advancement/retraction driving unit when the interference occurs on the basis of the information detected by the sensor.

In the method for controlling a medical manipulator of the present invention, when the treatment tool is driven in a direction in which the treatment tool is retracted from the overtube because an external force greater than or equal to a predetermined value acts on joints provided on the treatment tool, the controller may control the advancement/retraction driving unit on the basis of the information detected by the sensor.

In the method for controlling a medical manipulator of the present invention, position information of the treatment tool from the advancement/retraction driving unit may be stored in a storage unit as storage information, and the controller may perform control to stop advancement/retraction movement of the treatment tool according to a predetermined relationship with advanced/retracted position information of the treatment tool based on the storage information and the information detected by the sensor.

DETAILED DESCRIPTION OF THE INVENTION

Hereinafter, a first embodiment of the present invention will be described with reference to FIGS. 1 to 7.

Figure 1:
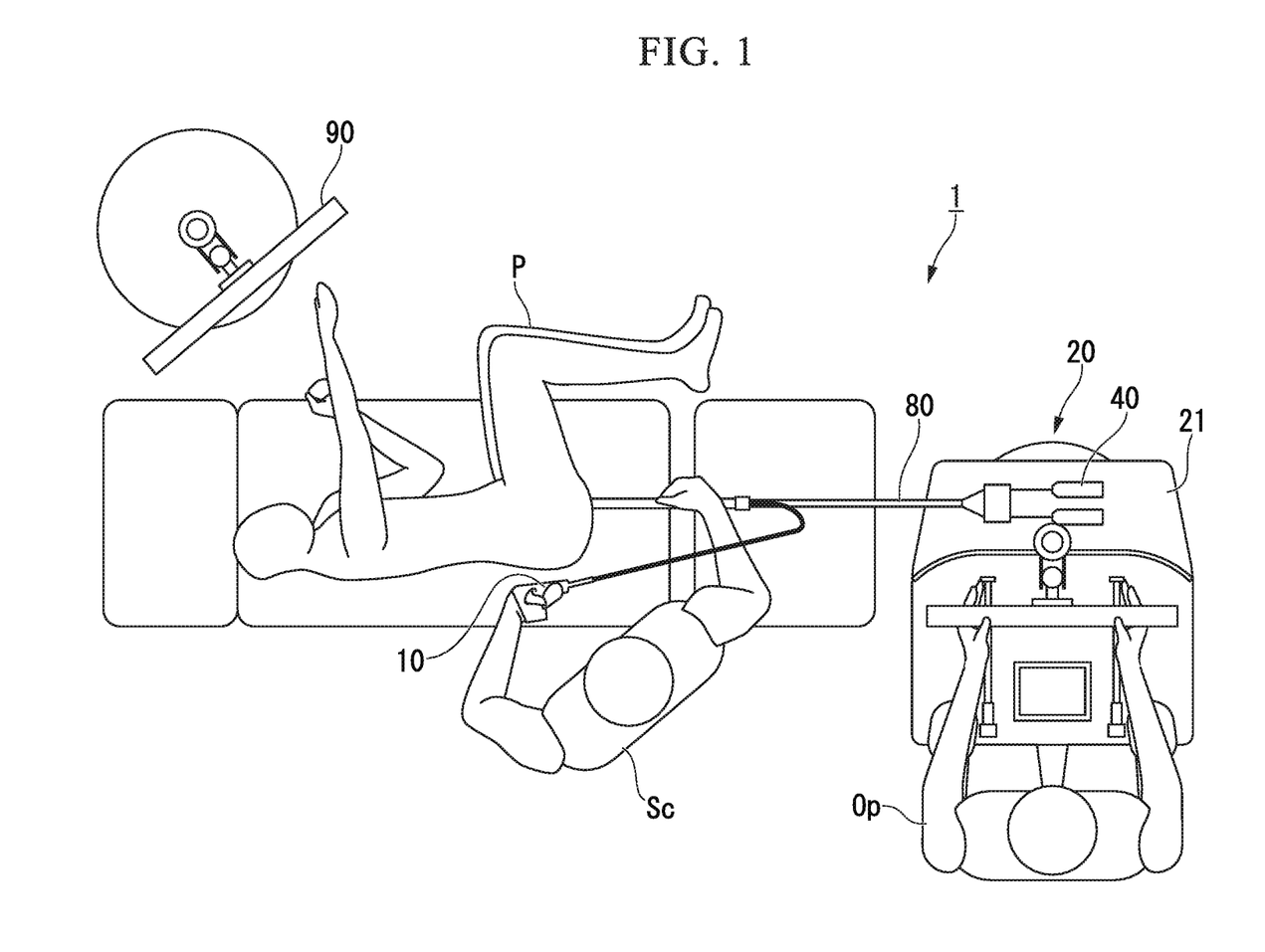
FIG. 1 is a diagram illustrating a medical manipulator system according to a first embodiment of the present invention.

FIG. 1 is a diagram illustrating a medical manipulator system (hereinafter referred to simply as a "system") 1 of the present embodiment. The system 1 includes an endoscope 10 for observing the interior of the body of a patient P, a medical manipulator (hereinafter referred to simply as a "manipulator") 20 for performing a procedure in the body of the patient P, and an overtube (an insertion aid device) 80 through which the endoscope 10 and the manipulator 20 are inserted.

The endoscope 10 can be appropriately selected from various known constitutions in consideration of performance, applications, and so on.

Although not illustrated, the overtube 80 has a first lumen through which the endoscope 10 is inserted, and a second lumen through which the manipulator 20 is inserted. The overtube 80 can also be appropriately selected and used from various known constitutions in consideration of dimensions, and so on. When an overtube configured to have a bendable part in the vicinity of a distal end thereof is used, it is easy to reach a target region in which a procedure is to be performed.

The manipulator 20 includes a console 21 manipulated by an operator Op, and a treatment tool unit 40 mounted on the console 21.

Figure 2:
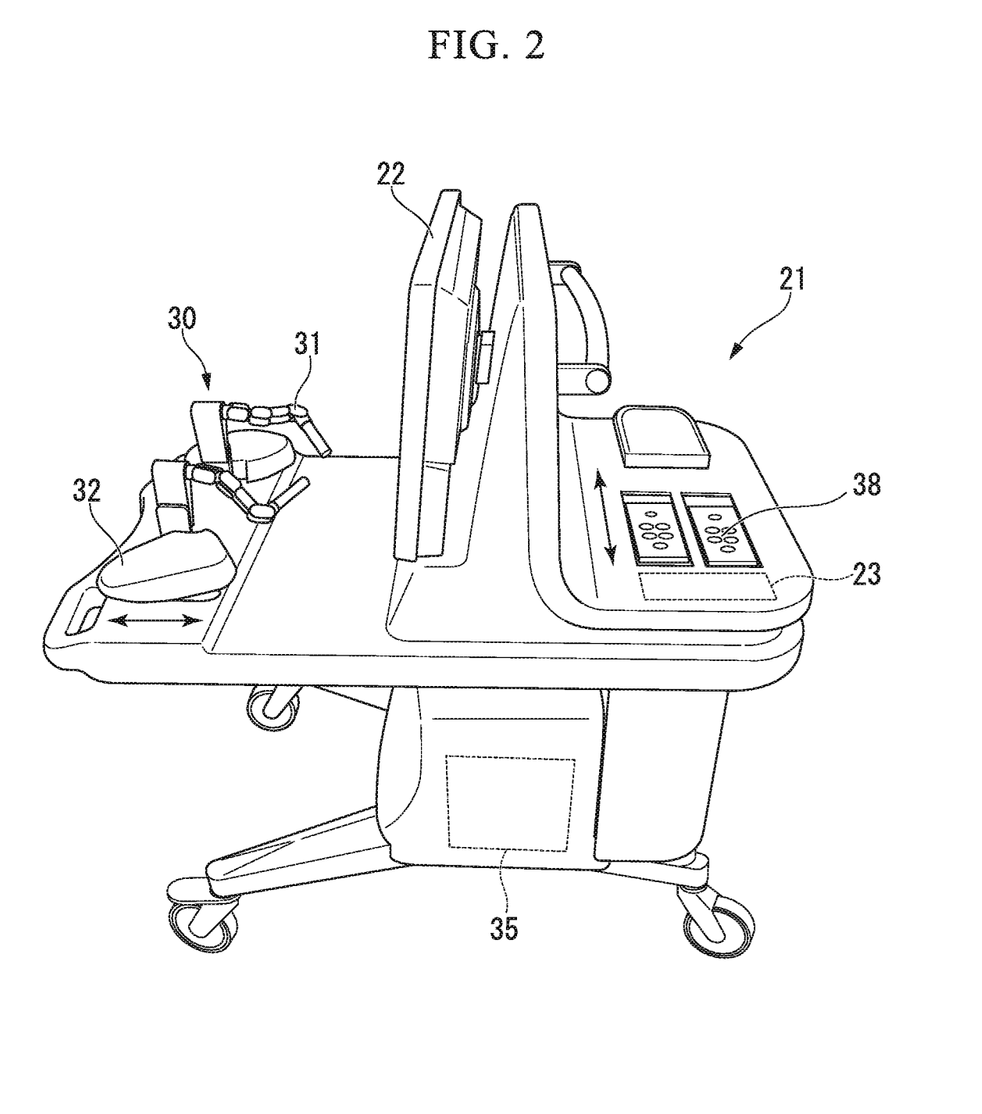
FIG. 2 is a diagram illustrating a console in the medical manipulator system.

FIG. 2 is a diagram illustrating the console 21. The console 21 includes a manipulation unit 30 that is manipulated and input by the operator Op, a control unit 35 that operates the treatment tool unit 40 on the basis of an output from the manipulation unit 30, a mounting unit (an advancement/retraction driving unit) 38 on which the treatment tool unit 40 is mounted, a monitor 22, and a stopper 23.

The monitor 22 is connected to the endoscope 10, and displays images acquired by the endoscope 10. Details of the stopper 23 will be described below.

Figure 3:
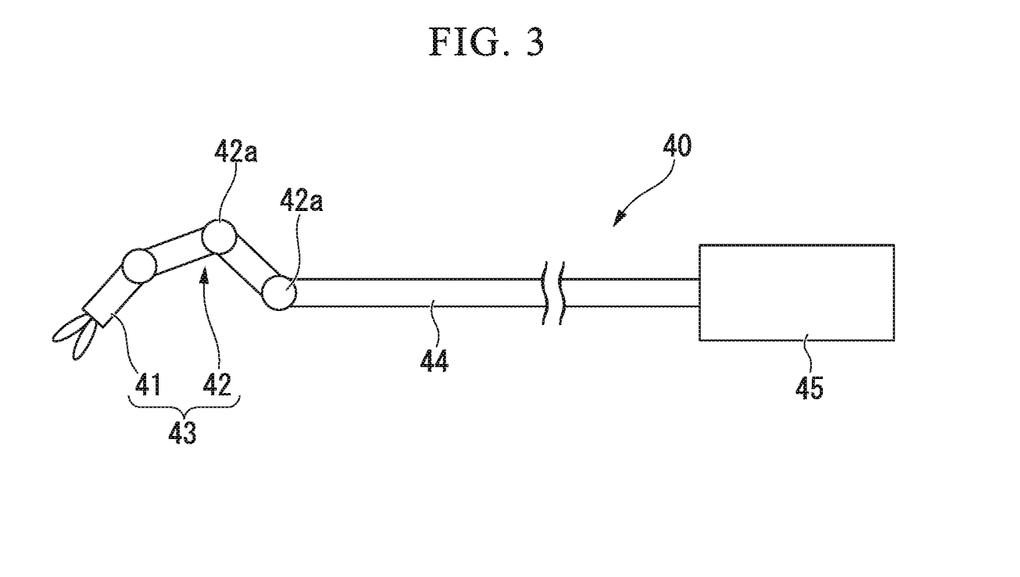
FIG. 3 is a schematic diagram illustrating a treatment tool unit in the medical manipulator system.

FIG. 3 is a diagram schematically illustrating the treatment tool unit 40. The treatment tool unit 40 includes an arm unit 43 that has a treatment tool (an end effector) 41 and an arm 42 on which the treatment tool 41 is mounted, and a motor unit 45 that drives the treatment tool 41 and the arm 42. An area between the arm 43 and the motor unit 45 serves as a connector 44 having flexibility.

Figure 4:
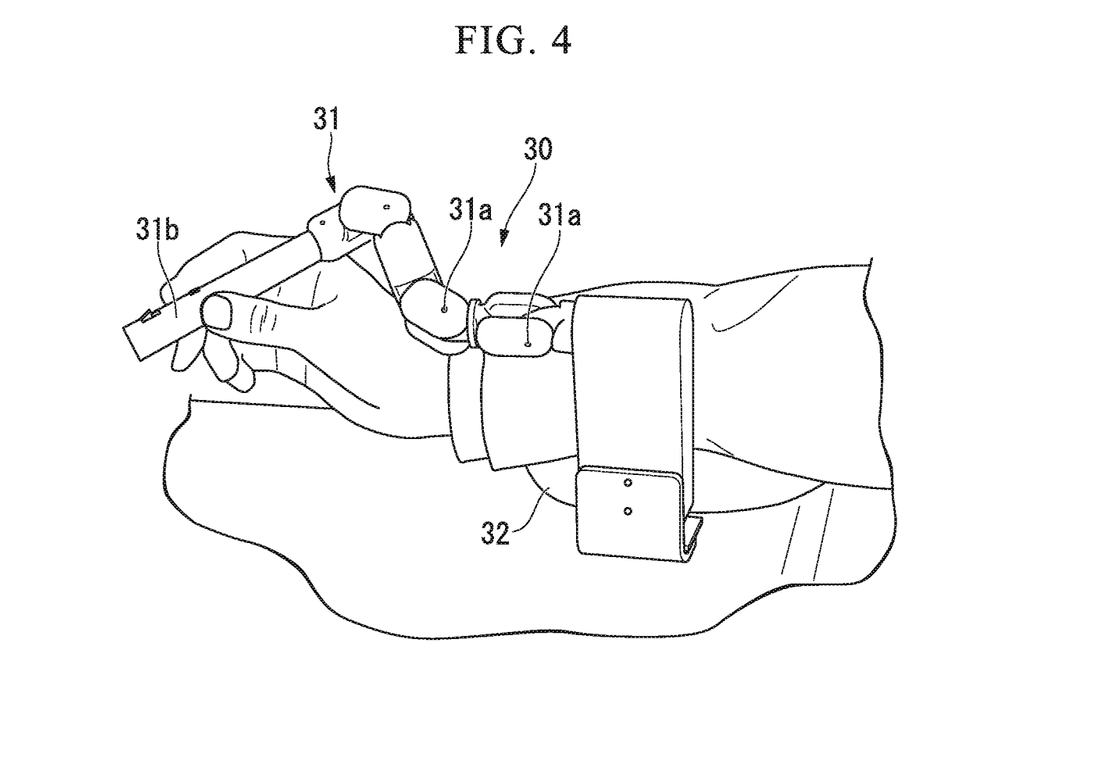
FIG. 4 is a diagram illustrating a manipulation unit in the console.

FIG. 4 is a diagram illustrating the manipulation unit 30 of the console 21. The manipulation unit 30 has a manipulation arm 31 that is used for manipulation input to the arm 42, and a base unit (advancement/retraction operation unit) 32 on which the manipulation arm 31 is mounted.

The manipulation arm 31 and the arm 42 of the treatment tool unit 40 have a plurality of joints 31a and a plurality of joints 42a. The number of joints 31a is equal to the number of joints 42a, and the joints pivot in the same way. An encoder (not shown) or the like is provided on each of the joints 31a and 42a, and is configured to be able to detect a rotation angle. Thereby, when the operator Op manipulates the manipulation arm 31 so that a shape of the manipulation arm 31 becomes an arbitrary shape, the joints 42a of the arm 42 are driven by the control unit 35, and a shape of the arm 43 becomes a shape corresponding to the shape of the manipulation arm 31.

A treatment manipulation unit 31b for operating the treatment tool 41 is provided at a distal end portion of the manipulation arm 31. A specific type of the treatment manipulation unit 31b can be appropriately set depending on, for instance, a constitution of the treatment tool 41. For example, when the treatment tool 41 is grasping forceps, it may have a structure equivalent to that of grasping forceps. When the treatment tool 41 is a knife to be used by being energized, the knife may have a structure having a button that switches the energization ON/OFF.

The base unit 32 is mounted to be movable relative to the console 21. When the base unit 32 is moved relative to the console 21, the mounting unit 38 moves relative to the console 21. Thereby, the treatment tool unit 40 mounted on the mounting unit 38 can be moved relative to the console 21.

Figure 5:
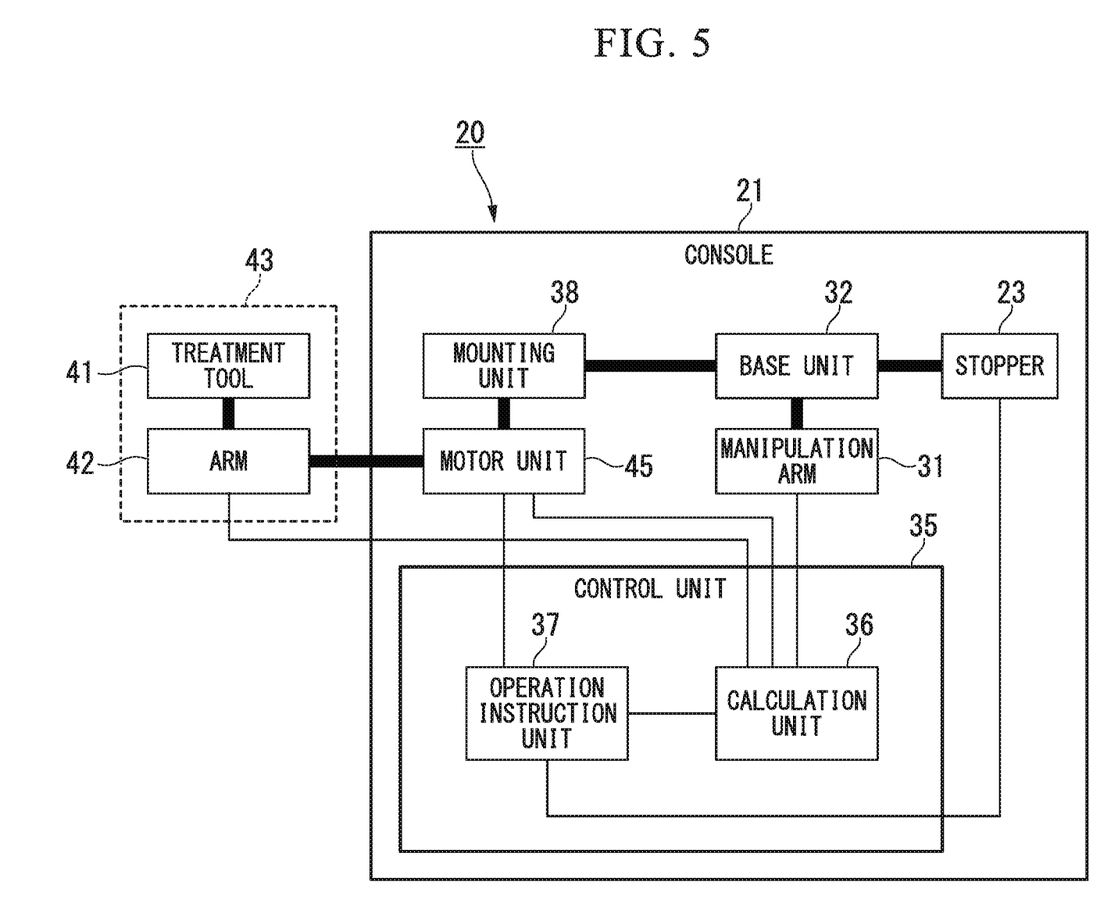
FIG. 5 is a functional block diagram of a medical manipulator in the medical manipulator system.

FIG. 5 is a functional block diagram of the manipulator 20 in a state in which the treatment tool unit 40 is mounted on the console 21. In FIG. 5, the monitor 22 is omitted. In FIG. 5, a thick line by which components are connected refers to a physical coupling that can transmit power, and a thin line by which components are connected refers to a logical coupling that can transceive a signal.

In the manipulator 20 of the present embodiment, the base unit 32 and the mounting unit 38 are physically coupled by, for instance, a belt or a chain. Therefore, when the base unit 32 is moved relative to the console 21, the mounting unit 38 moves relative to the console 21 in conjunction with the base unit 32. In this case, the manipulation arm 31 moves along with the base unit 32, and the motor unit 45 mounted on the mounting unit 38 also moves along with the mounting unit 38.

The stopper 23 is physically coupled with the base unit 32. When the stopper 23 is actuated, the base unit 32 is held so as not to move relative to the console 21.

The motor unit 45 is physically coupled with the arm 43. The motor unit 45 has a plurality of drive sources such as motors, and the joints 42a of the arm 42 are connected to the corresponding drive sources by transmitting members such as wires. The treatment tool 41 is also connected to the drive source by a transmitting member as needed.

The control unit 35 includes a calculation unit (an interference detection unit) 36 that performs various arithmetic operations and determinations, and an operation instruction unit 37 that is logically coupled with the calculation unit 36 and operates each unit of the manipulator 20 in response to output of the calculation unit 36.

The calculation unit 36 is logically coupled with the manipulation arm 31, the arm 42, and the motor unit 45. The operation instruction unit 37 is logically coupled with the motor unit 45 and the stopper 23, and is configured to be able to operate the motor unit 45 and the stopper 23 by transmitting an operation signal.

An operation of the system 1 configured as described above when the system 1 is used will be described using a case in which a procedure is performed on the large intestine as an example. As illustrated in FIG. 1, the system 1 is manipulated by at least two persons including an operator Op who manipulates the console 21 and an endoscopic technician Sc who manipulates the overtube 80 and the endoscope 10.

As a preparation task, the motor unit 45 of the treatment tool unit 40 is mounted on the mounting unit 38 of the console 21.

Next, as illustrated in FIG. 1, the endoscopic technician Sc inserts the endoscope 10 into the first lumen of the overtube 80, and inserts the treatment tool unit 40 into the second lumen from the arm 43 side of the treatment tool unit 40.

The endoscopic technician Sc inserts the overtube 80, into which the endoscope 10 and the treatment tool unit 40 have been inserted, into the anus of a patient P. Subsequently, the endoscopic technician Sc advances the overtube 80 into the large intestine while observing an image acquired by the endoscope 10 through the second monitor 90, and introduces the overtube 80 through which the endoscope 10 and the treatment tool unit 40 have been inserted to the neighborhood of a target region.

Subsequently, the endoscopic technician Sc projects the endoscope 10 out of the overtube 80, performs a bending manipulation as needed, and secures a visual field when a procedure is performed on the target region. Then, the preparatory tasks are completed.

After the preparatory tasks are completed, when the operator Op moves the base unit 32 ahead of him/her while grasping the manipulation arm 31, the mounting unit 38 and the motor unit 45 interlock with each other, and the treatment tool unit 40 moves toward a distal end of the overtube 80. As a result, the arm 43 is projected out of the overtube 80.

After the arm 43 is projected out of the overtube 80, the operator Op performs predetermined input to the manipulation unit 30 to associate the manipulation arm 31 with the arm 43. An associating instruction is output from the manipulation unit 30 to the control unit 35 on the basis of the predetermined input.

In the control unit 35 that receives the associating instruction, first, the calculation unit 36 acquires information that shows the states of the joints 31a of the manipulation arm 31 and information that shows the states of the joints 42a of the arm 42. Next, the calculation unit 36 calculates an operation amount of each joint 42a which is required to change the arm 42 into a shape similar to the manipulation arm 31, and transmits the calculated operation amount to the operation instruction unit 37.

The operation instruction unit 37 generates a driving signal for driving each joint 42a on the basis of the required operation amount of each joint 42a which has been received, and transmits the generated driving signal to the motor unit 45. The motor unit 45 is driven, and each joint 42a is operated. When the arm 42 and the manipulation arm 31 have approximately the same shape or a similar shape, the associating process is completed.

After the associating process is completed, the same processes as in this associating process are repeated at predetermined intervals (e.g., several tens of milliseconds). Thereby, the arm 43 on which the treatment tool 41 is mounted is subjected to similar control such that it maintains a shape similar to that of the manipulation arm 31.

The operator Op appropriately manipulates the manipulation arm 31 and the treatment manipulation unit 31b while checking an image of the target region which is displayed on the monitor 22, and can thereby perform a desired procedure on the target region.

Figure 6:
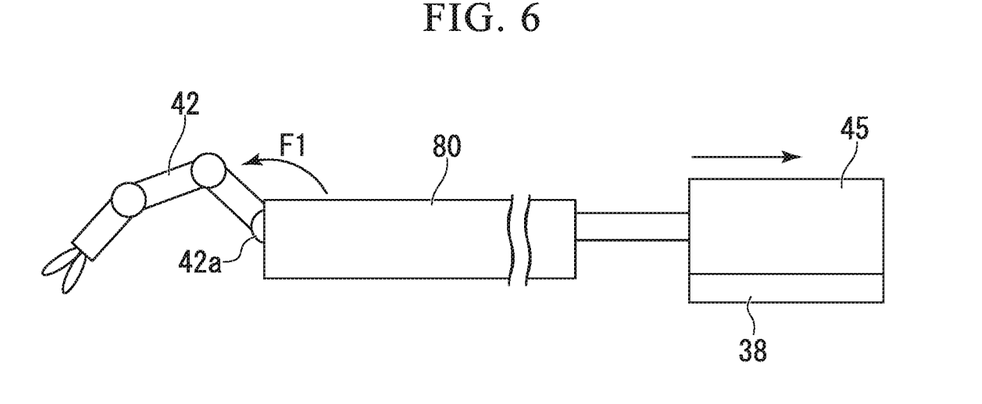
FIG. 6 is a diagram illustrating a state in which the treatment tool unit interferes with an overtube.

In case the operator Op causes the arm unit 43 retracted, the operator Op retracts the base unit 32 in front of him/her. In this case, as illustrated in FIG. 6, when the arm 42 is bent, the arm unit 43 cannot enter the second lumen of the overtube 80. In this state, when the retracting operation of the base unit 32 is continued, an excessive load is applied to the arm unit 43, and the arm unit 43 or the overtube 80 may be damaged.

The system 1 of the present embodiment is configured to prevent an excessive load from being applied to the arm unit 43 when the arm unit 43 and the overtube 80 interfere with each other. This will be described below in detail.

As illustrated in FIG. 6, it is assumed that the joint 42a disposed closest to the proximal end among the plurality of joints of the arm 42 is bent. In this state, when the operator Op retracts the base unit 32, an area closer to the distal end than the joint 42a cannot enter the overtube 80. As a result, the arm unit 43 and the overtube 80 interfere with each other.

When the base unit 32 is further retracted in the state in which the arm 43 and the overtube 80 interfere with each other, a force F1 acts on an area close to the distal end of the bent joint 42a by the overtube 80 in a direction parallel to an area close to the proximal end of the joint 42a.

Figure 7:
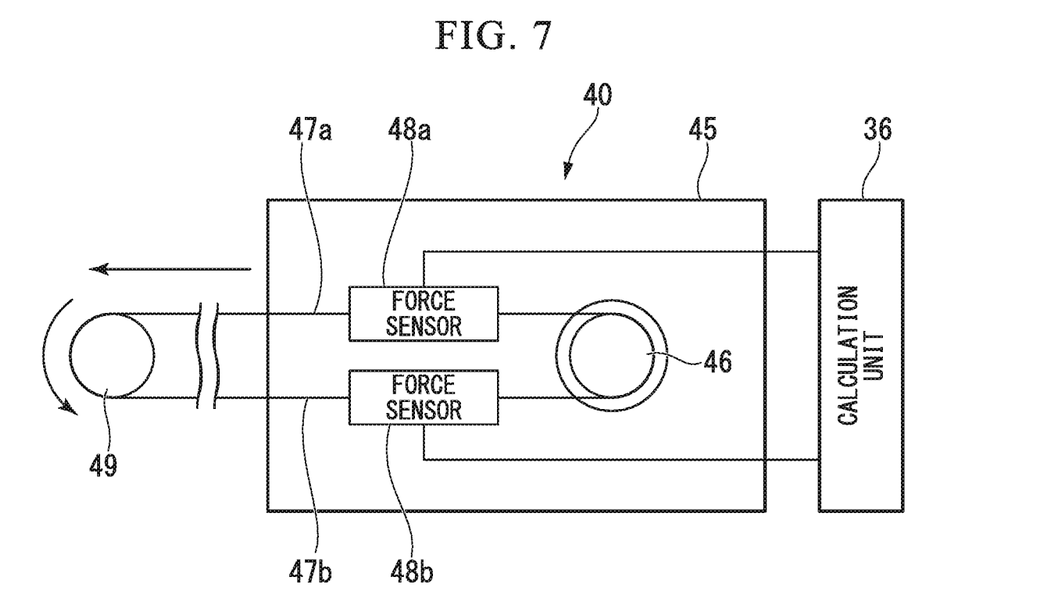
FIG. 7 is a schematic diagram illustrating a part of the treatment tool unit.

FIG. 7 is a schematic view illustrating a part of the treatment tool unit 40. A driving pulley 46 mounted on the drive source of the motor unit 45 and a driven pulley 49 for driving the joints 42a are connected by manipulating members 47a and 47b to be able to transmit a driving force.

When the force F1 acts on the joints 42a by the interference, the manipulating member 47a pulled by the driving pulley 46 to bend the joint 42a is pulled back toward the driven pulley 49. As a result, a tensile force acting on the manipulating member 47a increases.

Force sensor 48a is mounted on the manipulating member 47a. Force sensor 48b is mounted on the manipulating member 47b. Detected values of the force sensors 48a and 48b are transmitted to the calculation unit 36 of the control unit 35 at a predetermined interval. The calculation unit 36 determines that the arm 43 and the overtube 80 interfere with each other when the detected values of the force sensors 48a and 48b exceed a predetermined threshold, that is, an external force greater than or equal to a predetermined value acts on the joints 42a, and transmits the determined result to the operation instruction unit 37.

The operation instruction unit 37 receiving the determined result sends an operation signal to the stopper 23, and actuates the stopper 23. When the stopper 23 is actuated, the base unit 32 is held so as not to be movable relative to the console 21. As a result, movement of the mounting unit 38 relative to the console 21 is prevented, and the treatment tool unit 40 can be neither advanced nor retracted with respect to the overtube 80.

Thereby, the excessive load caused by the interference with the overtube 80 is prevented from acting on the arm 43.

The aforementioned force sensors are provided on all the joints of the arm 42, and detected values of all the force sensors are transmitted to the calculation unit 36 at a predetermined interval. The calculation unit 36 continuously monitors the presence or absence of the interference with respect to all the joints of the arm 42.

According to the system 1 of the present embodiment, when the calculation unit 36 detects the interference between the treatment tool unit 40 and the overtube 80, the operation instruction unit 37 actuates the stopper 23 to regulate the retraction of the treatment tool unit 40 with respect to the overtube 80. As a result, it is possible to suitably prevent the excessive load from acting on the arm 43, and to suppress damage or the like of the treatment tool unit 40.

In the system 1 of the present embodiment, since the joints 31a of the manipulation arm 31 are not driven by drive sources, even when a load caused by interference acts on the arm 43, the load is not fed back to the manipulation arm 31. Therefore, the operator Op cannot recognize, from the manipulation arm 31, that the load caused by interference acts on the arm 43.

Further, since the endoscope 10 is projected out of the overtube 80 during a procedure, the joints of the arm 43 at which the interference occurs are frequently located beyond a visual field of the endoscope 10. Therefore, it is also difficult for the operator Op to recognize, from the image displayed on the monitor 22, that the arm 43 and the overtube 80 interfere with each other.

In the system 1 configured as described above, it is very difficult to avoid the interference between the treatment tool unit and the overtube or to suppress an extent of the interference by means of proper manipulation of the operator Op.

The system 1 includes the calculation unit 36 and the operation instruction unit 37, so that damage or the like of the treatment tool unit can be reliably suppressed regardless of the manipulation of the operator Op.

The operation instruction unit 37 operates the stopper 23 when the calculation unit 36 determines that the interference occurs. Therefore, an effect of preventing the excessive load of the treatment tool unit in the system 1 is stably exhibited without being affected by a change in a relative position relationship caused, for instance, because the overtube 80 meanders in the body. As a result, an adverse effect of the interference between the arm and the overtube can be reliably suppressed although the overtube has flexibility.

In the present embodiment, numerous specific aspects of the stopper are considered. For example, the stopper may be a brake that fixes at least one of the base unit 32 and the mounting unit 38 so as not to move relative to the console 21, or a clutch that can release interlocking between the base unit 32 and the mounting unit 38. That is, the stopper may be provided on one or both of the advancement/retraction driving unit and the advancement/retraction operation unit or be provided at a position at which neither the advancement/retraction driving unit nor the advancement/retraction operation unit is present, as long as it can be actuated to regulate an operation of the advancement/retraction driving unit.

The interference between the arm 43 and the overtube 80 occurs when the treatment tool unit is retracted from the overtube. Therefore, the stopper needs only to at least regulate the retraction of the treatment tool unit from the overtube, and may be configured to permit the advance from the overtube.

Further, the system 1 may be configured such that a predetermined message or sign is displayed on the monitor 22 when the stopper 23 is operated to enable the operator Op to easily recognize that the stopper 23 is operated.

Further, the constitution for detecting the interference is not limited to the aspect using the aforementioned force sensors. For example, in a case in which the motor unit uses a servo motor as the drive source, when the joints are rotated by the external force generated by the interference with the overtube, a current value which the drive source outputs varies to maintain the joints at a predetermined rotation angle. Therefore, the system may be configured such that the calculation unit determines the presence or absence of the interference by whether or not a difference between a current value which the operation instruction unit instructs to the drive source and a current value that is actually detected by the drive source is greater than or equal to a predetermined threshold.

A second embodiment of the present invention will be described with reference to FIG. 8. The present embodiment is different from the first embodiment in an aspect in which it is determined whether or not the interference occurs. In the following description, the components common with those described above are given the same reference signs, and duplicate description thereof will be omitted.

Figure 8:
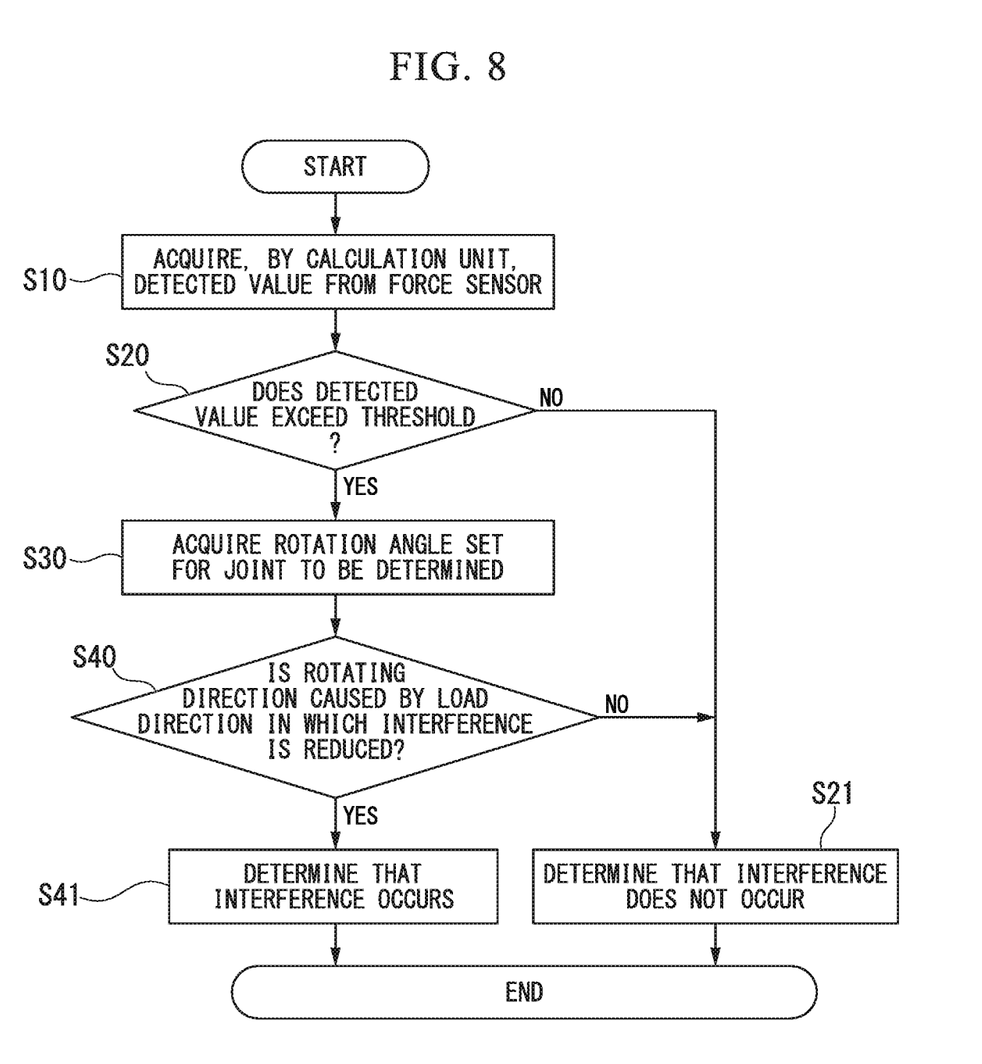
FIG. 8 is a flowchart illustrating a flow of determination of the presence or absence of interference in a medical manipulator system according to a second embodiment of the present invention.

FIG. 8 is a flowchart illustrating a flow of determination of the calculation unit 36 in the system of the present embodiment.

In step S10, when the calculation unit 36 acquires a detected value from a force sensor (e.g., a force sensor 48a), the calculation unit 36 determines whether or not the detected value exceeds a threshold in step S20.

When the determination in step S20 is NO, the process proceeds to step S21, and the calculation unit 36 determines that no interference occurs, and the process is terminated. When the determination in step S20 is YES, the process proceeds to step S30.

In step S30, the calculation unit 36 makes reference to an operation signal which the operation instruction unit 37 transmits to a joint (a joint to be determined) that indicates a detected value that exceeds the threshold, and acquires a rotation angle set for the joint by the operation signal.

Next, in step S40, the calculation unit 36 specifies a direction in which a load generating the detected value that exceeds the threshold rotates the joint to be determined on the basis of the rotation angle acquired in step S30 and the detected value acquired in step S10, and determines whether or not a rotating direction, that is, a direction in which a load acts on the joint is a direction in which the interference is reduced.

When the arm 43 interferes with the overtube 80, the joint 43a pressed against the overtube 80 tends to rotate such that an area closer to the distal end than the joint 43a becomes parallel to the overtube 80, that is, in a direction in which the interference is reduced. Therefore, when the determination in step S40 is YES, the process proceeds to step S41, the calculation unit 36 determines that the interference occurs, and notifies the occurrence of the interference to the operation instruction unit 37, and terminates the process. When the determination in step S40 is NO, the process proceeds to step S21, the calculation unit 36 determines that the interference does not occur, and terminates the process. When the determination in step S40 is NO, it is thought that the load that generates the detected value exceeding the threshold is highly likely caused by, for instance, the arm 43 receiving a pressing force in contact with an organ or tissue, and is not at least caused by the overtube 80.

Like the first embodiment, the system of the present embodiment can also appropriately prevent the excessive load from acting on the arm 43, and suppress damage or the like of the treatment tool unit.

Further, since the calculation unit 36 is configured to determine whether or not the interference occurs in consideration of a direction of the load in addition to a magnitude of the load in the joint to be determined, an unnecessary actuation of the stopper can be suppressed by reducing erroneous determination regarding whether or not the interference occurs.

A third embodiment of the present invention will be described with reference to FIGS. 9 and 10. The present embodiment is different from each of the above embodiments in an aspect in which it is determined whether or not the interference occurs.

Figure 9:
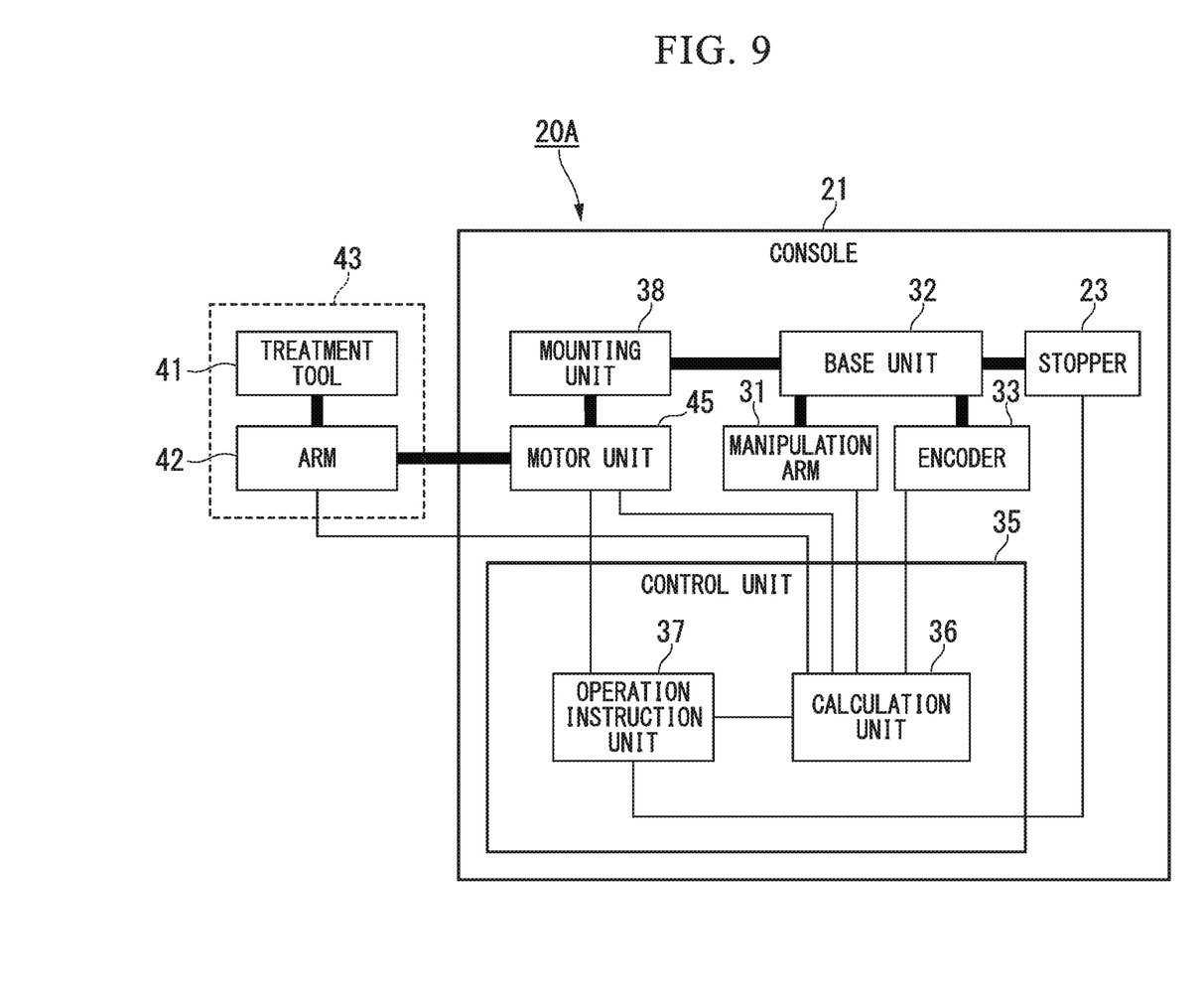
FIG. 9 is a functional block diagram of a medical manipulator in a medical manipulator system according to a third embodiment of the present invention.

FIG. 9 is a functional block diagram of a manipulator 20A in a system of the present embodiment. In the manipulator 20A, an encoder 33 is mounted on a base unit 32. The encoder 33 is logically coupled with a calculation unit 36, and the manipulator 20A is configured such that information about a positional relationship between the base unit 32 and a console 21, a moving direction of the base unit 32 relative to the console 21, etc. is transmitted to the calculation unit 36 at predetermined intervals.

Figure 10:
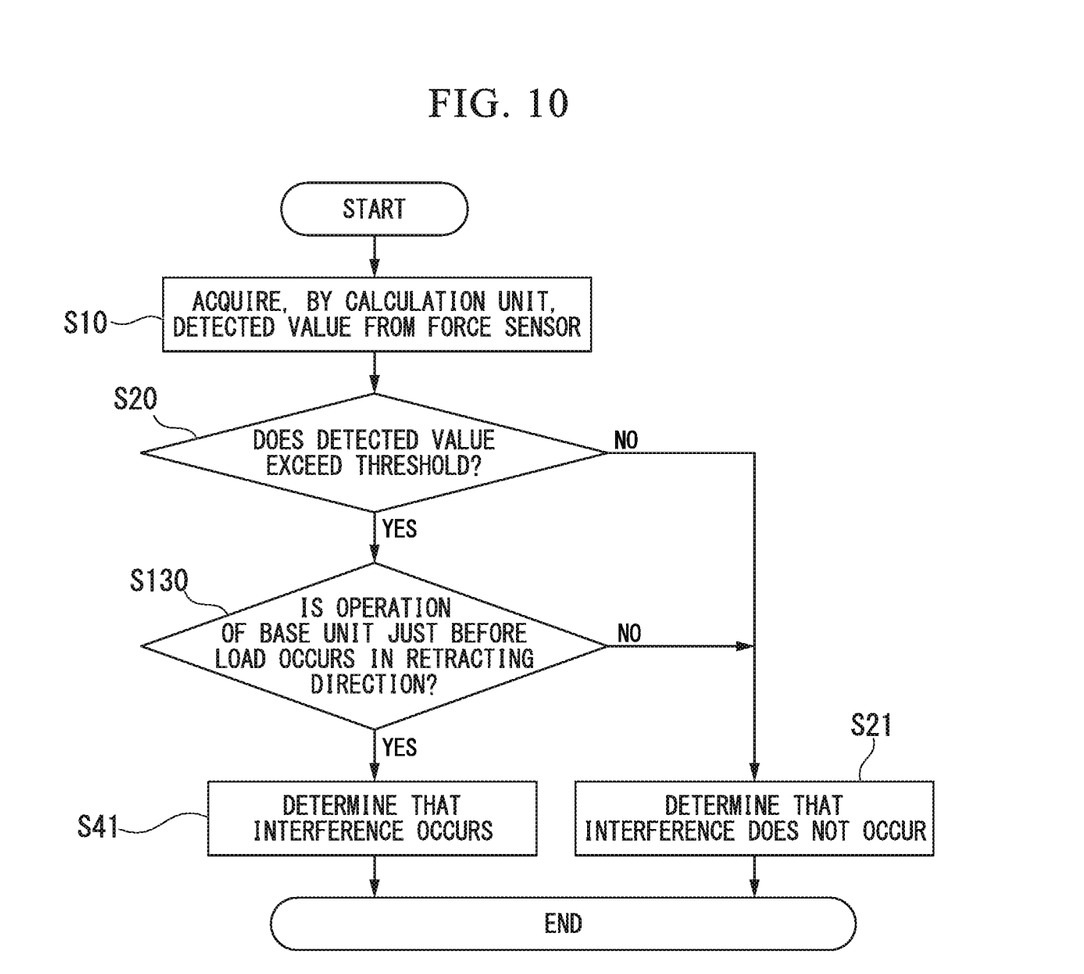
FIG. 10 is a flowchart illustrating a flow of determination of the presence or absence of interference in the medical manipulator system.

FIG. 10 is a flowchart illustrating a flow of determination of the calculation unit 36 in the system of the present embodiment. When determination in step S20 is YES, a process proceeds to step S130 in place of step S30.

In step S130, the calculation unit 36 determines, on the basis of information acquired from the encoder 33, whether or not an operation of the base unit 32 just before a load exceeding a threshold occurs is movement in front of an operator Op. This determination is performed to determine whether or not a mounting unit 38 interlocking with the base unit 32 is driven in a direction in which it retracts a mounted treatment tool unit 40 with respect to an overtube 80. When the determination in step S130 is YES, the process proceeds to step S41. When the determination is NO, the process proceeds to step S21. The other points are the same as in the second embodiment.

Like the system of each of the above embodiments, the system of the present embodiment which includes the manipulator 20A can also appropriately prevent an excessive load from acting on an arm unit 43, and suppress damage or the like of the treatment tool unit.

Further, since the calculation unit 36 is configured to determine whether or not the interference occurs in consideration of a moving direction of the base unit 32 in addition to a magnitude of a load in a joint to be determined, an unnecessary actuation of a stopper can be suppressed by reducing erroneous determination regarding whether or not the interference occurs.

In the present embodiment, the encoder 33 may be mounted on the mounting unit 38 instead of the base unit 32, or may be mounted on both the base unit 32 and the mounting unit 38.

While the embodiments of the present invention have been described, the technical scope of the present invention is not limited to the above embodiments, and the present invention can change a combination of the components, variously modify each component, or delete each component without departing from the spirit or teaching of the present invention.

Figure 11:
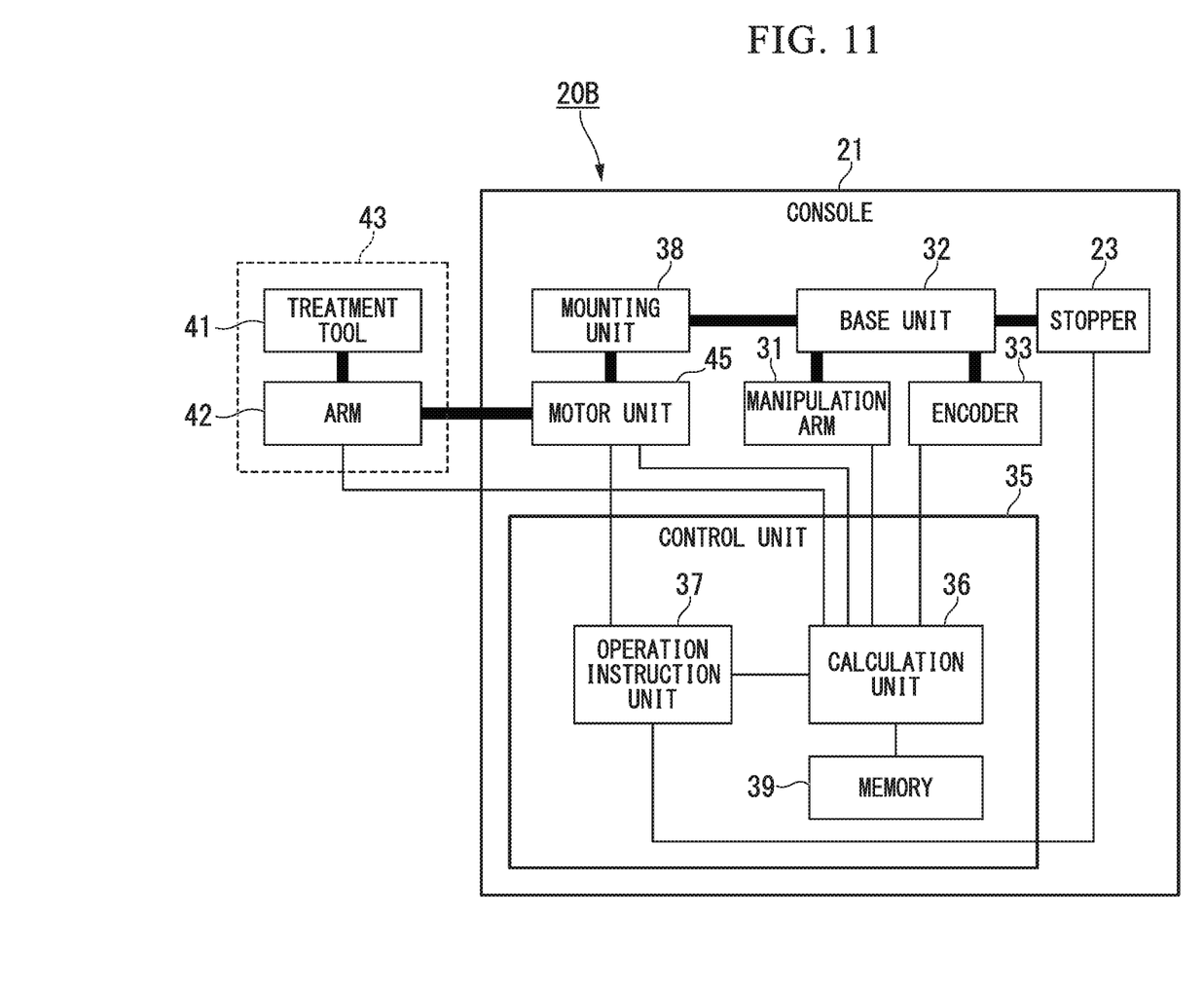
FIG. 11 is a functional block diagram of a medical manipulator in a medical manipulator system according to a modification of the present invention.

For example, as illustrated in FIG. 11, a system of a modification may be configured using a manipulator 20B that includes an encoder (an advanced/retracted position detector) 33 that is disposed at at least one of a base unit 32 and a mounting unit 38, and a memory (a storage unit) 39 that is provided on a control unit 35 and is logically coupled with a calculation unit 36.

In this case, the calculation unit 36 acquires information (advanced/retracted position information) indicating a relative position of the mounting unit 38 relative to a console 21 from the encoder 33 at a point in time when the calculation unit 36 determines that interference between a treatment tool unit and an overtube occurs, and stores the acquired information in the memory 39. Afterward, when advanced/retracted position information of the mounting unit 38 which is acquired from the encoder 33 satisfies a predetermined relationship with respect to the advanced/retracted position information stored in the memory 39, the system may be configured such that an operation instruction unit 37 actuates a stopper 23 regardless of a result of determining the presence or absence of the interference.

With this constitution, after the interference occurs once, retraction of the treatment tool unit 40 can be regulated before the interference occurs, and a load acting on an arm unit can be further reduced.

In this modification, the aforementioned predetermined relationship for actuation of the stopper after the interference occurs once can be appropriately set. Therefore, the predetermined relationship may be limited to only the same position as a position at which the interference occurs, or be set to widen a range from the position at which the interference occurs to the vicinity of the proximal end to the degree of several millimeters to more reliably avoid the occurrence of the interference.

Like the above embodiments, the system may be configured such that the calculation unit 36 determines whether or not the interference occurs prior to actuating the stopper 23, and the actuation of the stopper 23 is cancelled when it is determined that the interference does not occurs. With this constitution, the system can be more accurately operated by reducing errors in the determination regarding whether or not the interference occurs.

The medical manipulator in the present invention is not limited to performing the similarity control as described above. For example, the medical manipulator may be a master-slave type medical manipulator with a master arm having a shape different from that of the arm.

In the present invention, the end effector is not limited to the treatment tool. For example, the end effector may be observation means for enlarging and observing apart of the target region.

The invention claimed is:

1. A medical manipulator system comprising:
a treatment tool including an arm having at least one joint and an end effector provided at a distal end of the arm;
a lumen through which the treatment tool is inserted;
a slave device configured to drive the treatment tool to be advanced/retracted in a longitudinal axis direction of the lumen;
a master device configured to drive the slave device to advance/retreat the treatment tool in the longitudinal axis direction;
a stopper configured to limit movement of the slave device and a corresponding retraction of the treatment tool in the longitudinal axis direction;
an interference sensor configured to detect an interference between the arm projected from a distal end of the lumen with the distal end of the lumen; and
a controller comprising hardware, the controller being configured to actuate the stopper to limit the movement of the slave device and the corresponding retraction of the treatment tool with respect to the distal end of the lumen in response to the interference sensor detecting the interference.

2. The medical manipulator system according to claim 1, wherein the interference sensor is configured to determine that the interference occurs in response to an external force greater than or equal to a predetermined value acting on the at least one joint in a direction in which the external force reduces the interference.

3. The medical manipulator system according to claim 1, wherein the interference sensor is configured to determine that the interference occurs in response to an external force greater than or equal to a predetermined value acting on the at least one joint in response to the slave device being driven in a direction in which the slave device retracts the treatment tool with respect to the distal end of the lumen.

4. The medical manipulator system according to claim 1, wherein the interference sensor is configured to determine that the interference occurs in response to an external force greater than or equal to a predetermined value acting on the at least one joint.

5. The medical manipulator system according to claim 1, further comprising:
an advanced/retracted position sensor configured to detect a position of the slave device; and
a memory configured to store advanced/retracted position information detected by the advanced/retracted position sensor,
wherein the interference sensor stores the advanced/retracted position information in the memory in response to the interference being detected, and
the controller actuates the stopper in response to advanced/retracted position information subsequently acquired by the advanced/retracted position sensor satisfying a predetermined relationship with respect to the advanced/retracted position information stored in the member.

6. A medical manipulator system comprising:
a treatment tool including an arm having at least one joint and an end effector provided on the arm;
a lumen through which the treatment tool is inserted;
a slave device configured to drive the treatment tool to be advanced/retracted in a longitudinal axis direction of the lumen;
a master device configured to drive the slave device to advance/retreat the treatment tool in the longitudinal axis direction;
a stopper configured to limit movement of the slave device and a corresponding retraction of the treatment tool in the longitudinal axis direction;
a force sensor configured to detect an interference between the arm projected from a distal end of the lumen with the distal end of the lumen; and
a controller comprising hardware, the controller being configured to operate the stopper to limit the movement of the slave device and the corresponding retraction of the treatment tool with respect to the distal end of the lumen in response to the force sensor detecting the interference.

7. The medical manipulator system according to claim 6, wherein the force sensor is configured to determine that the interference occurs in response to an external force greater than or equal to a predetermined value acting on the at least one joint in a direction in which the external force reduces the interference.

8. The medical manipulator system according to claim 6, wherein the force sensor is configured to determine that the interference occurs in response to an external force greater than or equal to a predetermined value acting on the at least one joint in response to the slave device being driven in a direction in which the slave device retracts the treatment tool with respect to the distal end of the lumen.

9. The medical manipulator system according to claim 6, wherein the force sensor is configured to determine that the interference occurs in response to an external force greater than or equal to a predetermined value acting on the at least one joint.

10. The medical manipulator system according to claim 6, further comprising:
an advanced/retracted position sensor configured to detect a position of the slave device; and
a memory configured to store advanced/retracted position information detected by the advanced/retracted position sensor,
wherein the force sensor stores the advanced/retracted position information in the memory in response to the interference being detected, and
the controller actuates the stopper in response to advanced/retracted position information subsequently acquired by the advanced/retracted position sensor satisfying a predetermined relationship with respect to the advanced/retracted position information stored in the memory.

11. A method for controlling a medical manipulator, the method comprising:

detecting an interference between an arm of a treatment tool with a distal end of a lumen through which the treatment tool is inserted in response to the treatment tool being retracted relative to the distal end of the lumen; and controlling a slave device, which drives the treatment tool to be advanced/retracted in the lumen, to limit retraction of the treatment tool relative to the distal end of the lumen in response to the interference being detected.

12. The method according to claim 11, wherein the detecting comprises detecting an external force greater than or equal to a predetermined value acting on at least one joint provided on the treatment tool in a direction in which the external force reduces the interference between the at least one joint and the distal end of the lumen.

13. The method according to claim 11, wherein the detecting comprises detecting the treatment tool being driven in a direction in which the treatment tool is retracted from the lumen and causes an external force greater than or equal to a predetermined value to act on at least one joint provided on the treatment tool.

14. The method according to claim 11, further comprising storing position information of the slave device, wherein the controlling comprises limiting the retraction based on the position information and the detecting.

* * * * *